(12) United States Patent
Markle et al.

(10) Patent No.: US 8,110,251 B2
(45) Date of Patent: Feb. 7, 2012

(54) METHOD FOR POLYMERIZING A MONOMER SOLUTION WITHIN A CAVITY TO GENERATE A SMOOTH POLYMER SURFACE

(75) Inventors: David R. Markle, Berwyn, PA (US); Huashi Zhang, San Diego, CA (US); Matthew A. Romey, Newport Beach, CA (US); Ritchie A. Wessling, Watsonville, CA (US)

(73) Assignee: Glumetrics, Inc., Irvine, CA (US)

( * ) Notice: Subject to any disclaimer, the term of this patent is extended or adjusted under 35 U.S.C. 154(b) by 1038 days.

(21) Appl. No.: 12/026,396

(22) Filed: Feb. 5, 2008

(65) Prior Publication Data
US 2008/0187655 A1    Aug. 7, 2008

Related U.S. Application Data

(60) Provisional application No. 60/888,475, filed on Feb. 6, 2007.

(51) Int. Cl.
*B05D 3/10* (2006.01)

(52) U.S. Cl. ......... 427/336; 427/258; 427/350; 427/508
(58) Field of Classification Search .................. 427/258, 427/350, 508, 336
See application file for complete search history.

(56) References Cited

U.S. PATENT DOCUMENTS 5,618,587 A    4/1997  Markle et al.

FOREIGN PATENT DOCUMENTS

WO    WO 03/034047 A    4/2003

OTHER PUBLICATIONS

International Search Report, International Application No. PCT/US2008/053097.

*Primary Examiner* — Dah-Wei Yuan
*Assistant Examiner* — Robert S Walters, Jr.
(74) *Attorney, Agent, or Firm* — Knobbe, Martens, Olson & Bear, LLP (57) ABSTRACT

In preferred embodiments, the present invention relates to methods for polymerizing a monomer solution within a cavity covered by a porous membrane to generate a smooth polymer surface. More specifically, the method can be used to provide a medical device or sensor with a smooth polymer surface.

10 Claims, 5 Drawing Sheets

METHOD FOR POLYMERIZING A MONOMER SOLUTION WITHIN A CAVITY TO GENERATE A SMOOTH POLYMER SURFACE

CROSS-REFERENCE TO RELATED APPLICATIONS

This application claims the priority benefit to U.S. Provisional No. 60/888,475 filed Feb. 6, 2007, the entirety of which is hereby incorporated by reference herein.

BACKGROUND OF THE INVENTION

1. Field of the Invention

In preferred embodiments, the present invention relates to methods for polymerizing a monomer solution within a cavity such that the outer surface of the cavity has a smooth surface. More specifically, methods are disclosed for making a sensor comprising functional chemistry immobilized within a polymeric matrix disposed within a cavity along the sensor, wherein the sensor has a smooth outer surface.

2. Description of the Related Art

Polymers are widely used for coating surfaces in a wide variety of applications. For example, polymers are used to coat metals, fabrics, paper and glass to provide corrosion resistance, water resistance and insulation. With respect to biomedical applications, polymers can be used to increase the biocompatibility of a surface or to provide other desirable properties, such as immobilizing functional chemistries for intravascular deployment.

A variety of surface coating methods exist. One method involves dipping the surface to be treated in a solution or emulsion of a polymer and then either letting it dry or transferring the surface into a coagulation bath which is capable of extracting the solvent from the polymer solution. If the coat needs to be made thicker, the process can be repeated to add another layer of polymer to the coated surface.

In another method, the polymer is formed into a powder that is electrostatically sprayed onto a neutrally or oppositely charged surface. The charged polymer powder particles electrostatically adhere onto the surface. Heat treatment of the powdered surface cures and finishes the coated surface.

In another method, the surface is heated and immersed in a fluidized bed of powdered polymer particles. The fluidized bed of polymer particles is formed by aerating a bed of polymer particles with a gas. The powder adheres to the heated surface, which is then removed from the fluidized bed and further heated to cure and finish the coated surface.

There remains an unmet need for methods of making an analyte sensor, by immobilizing function chemistries in a polymeric matrix within a cavity in the sensor, such that the chemistries retain their functionality and wherein the outer surface of the sensor is smooth and non-thrombogenic.

SUMMARY OF THE INVENTION

A method is disclosed for making an analyte sensor having a smooth outer surface. The method comprises the steps of: providing an optical fiber comprising a cavity covered by a membrane having pores; loading the cavity and the membrane pores with a solution comprising polymerizable monomers, an analyte indicator system and a polymerization initiator; and initiating polymerization of the monomers.

In a preferred variation, prior to initiating polymerization, the loaded cavity and membrane pores are coated with wax and the solution is deoxygenated. In a further variation, the wax coating is removed after polymerization is completed to leave a smooth outer surface, wherein the analyte indicator system is immobilized within the cavity. Removing the wax may comprise contacting the wax with an organic solvent. Preferably the organic solvent is hexane. In another variation, the step of removing the wax may further comprise application of ultrasonic energy.

In one embodiment, the indicator system comprises a fluorophore and an analyte binding moiety.

In one embodiment, the loading step comprises vacuum filling.

In one embodiment, initiating polymerization comprises application of a second initiator selected to undergo a redox reaction with the first initiator.

In other embodiments, initiating polymerization comprises application of thermal or radiation (e.g., UV) energy.

DETAILED DESCRIPTION

Figure 1:
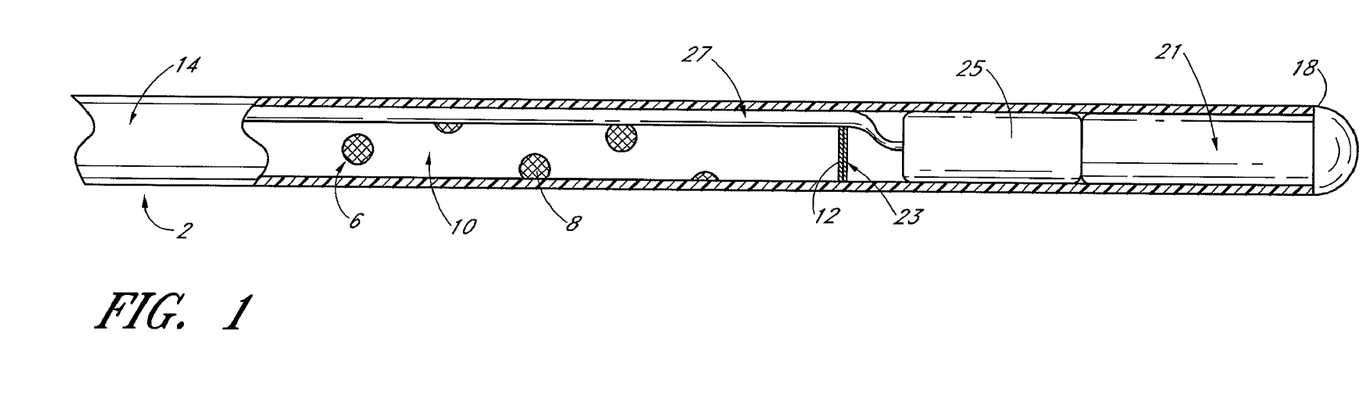
FIG. 1 is a cut-away view of a sensor where a portion of the porous membrane sheath is cut away to expose the optical fiber and hydrogel beneath the membrane.
Figure 2:
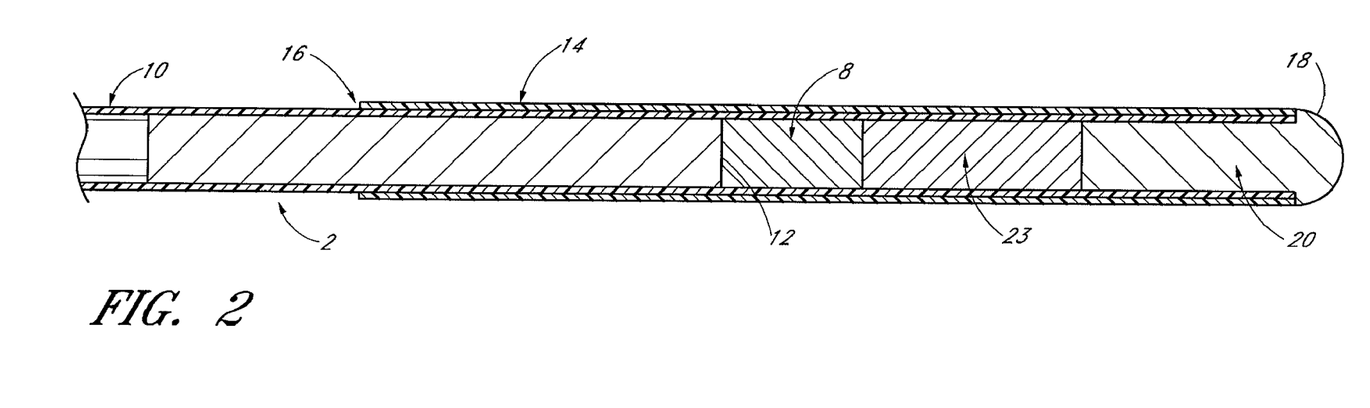
FIG. 2 is a cross-sectional view along a longitudinal axis of a sensor with a hydrogel disposed distal the optical fiber.

FIG. 1 shows a sensor 2 comprising an optical fiber 10 with a distal end 12 disposed in a porous membrane sheath 14. The optical fiber 10 has cavities 6, such as holes, in the fiber optic wall that can be formed by, for example, mechanical means such as drilling or cutting. The cavities 6 in the optical fiber 10 can be filled with a suitable compound, such as a polymer. In some embodiments, the polymer is a hydrogel 8. In other embodiments of the sensor 2 as shown in FIG. 2, the optical fiber 10 does not have cavities 6, and instead, the hydrogel 8 is disposed in a space distal to the distal end 12 of the optical fiber 10 and proximal to the mirror 23. In some embodiments, the sensor 2 is a glucose sensor. In some embodiments, the glucose sensor is an intravascular glucose sensor.

In some embodiments, the porous membrane sheath 14 can be made from a polymeric material such as polyethylene, polycarbonate, polysulfone or polypropylene. Other materials can also be used to make the porous membrane sheath 14 such as zeolites, ceramics, metals, or combinations of these materials. In some embodiments, the porous membrane sheath 14 is microporous and has a mean pore size that is less than approximately two nanometers. In other embodiments, the porous membrane sheath 14 is mesoporous and has a mean pore size that is between approximately two nanometers to approximately fifty nanometers. In still other embodiments, the porous membrane sheath 14 is macroporous and has a mean pore size that is greater than approximately fifty nanometers.

In some embodiments as shown in FIG. 2, the porous membrane sheath 14 is attached to the optical fiber 10 by a connector 16. For example, the connector 16 can be an elastic collar that holds the porous membrane sheath 14 in place by exerting a compressive force on the optical fiber 10. In other embodiments, the connector 16 is an adhesive or a thermal weld.

In some embodiments as shown in FIG. 1, a mirror 23 and thermistor 25 can be placed within the porous membrane sheath 14 distal the distal end 12 of the optical fiber 10. Thermistor leads 27 can be made to run in a space between the optical fiber 10 and porous membrane sheath 14. Although a thermistor 25 is shown, other devices such as a thermocouple, pressure transducer, an oxygen sensor, a carbon dioxide sensor or a pH sensor for example can be used instead.

In some embodiments as shown in FIG. 2, the distal end 18 of the porous membrane sheath 14 is open and can be sealed with, for example, an adhesive 20. In some embodiments, the adhesive 20 can comprise a polymerizable material that can fill the distal end 18 and then be polymerized into a plug. Alternatively, in other embodiments the distal end 18 can be thermally welded by melting a portion of the polymeric material on the distal end 18, closing the opening and allowing the melted polymeric material to resolidify. In other embodiments as shown in FIG. 1, a polymeric plug 21 can be inserted into the distal end 18 and thermally heated to weld the plug to the porous membrane sheath 14. Themoplastic polymeric materials such as polyethylene, polypropylene, polycarbonate and polysulfone are particularly suited for thermal welding. In other embodiments, the distal end 18 of the porous membrane sheath 14 can be sealed against the optical fiber 10.

After the porous membrane sheath 14 is attached to the optical fiber 10 and the distal end 18 of the porous membrane sheath 14 is sealed, the sensor 2 can be vacuum filled with a first solution 15 comprising a monomer, a crosslinker and a first initiator. Vacuum filling of a polymerizable solution through a porous membrane and into a cavity in a sensor is described in detail in U.S. Pat. No. 5,618,587 to Markle et al.; incorporated herein in its entirety by reference thereto. The first solution 15 is allowed to fill the cavity 6 within the optical fiber 10. In addition, as shown in FIG. 3A, the first solution 15 can also fill the void volume within the porous membrane sheath 14 which comprises pores 17 and channels 19 that are capable of being filled with the first solution 15.

In some embodiments, the first solution 15 is aqueous and the monomer, the crosslinker and the first initiator are soluble in water. For example, in some embodiments, the monomer is acrylamide, the crosslinker is bisacrylamide and the first initiator is ammonium persulfate. In other embodiments, the monomer is dimethylacrylamide or N-hydroxymethylacrylamide. By increasing the concentrations of the monomer and/or crosslinker, the porosity of the resulting gel can be decreased. Conversely, by decreasing the concentrations of the monomer and/or crosslinker, the porosity of the resulting gel can be increased. Other types of monomers and crosslinkers are also contemplated. In other embodiments, the first solution 15 further comprises an analyte indicator system comprising a fluorophore and an analyte binding moiety that functions to quench the fluorescent emission of the fluorophore by an amount related to the concentration of the analyte. In some embodiments, the fluorophore and analyte binding moiety are immobilized during polymerization, such that the fluorophore and analyte binding moiety are operably coupled. In other embodiments, the fluorophore and analyte binding moiety are covalently linked. The indicator system chemistry may also be covalently linked to the polymeric matrix. Some preferred fluorophores include HPTS-triLys-MA and HPTS-triCys-MA, and some preferred analyte binding quencher moieties include 3,3'-oBBV and derivatives thereof; these and other fluorophores and quenchers are described in detail in U.S. Provisional Application No. 60/833,081 and U.S. patent application Ser. No. (11/671,880), entitled OPTICAL DETERMINATION OF pH AND GLUCOSE, filed on the same day as the present application; these disclosures are incorporated herein by reference in their entirety.

Figure 4:
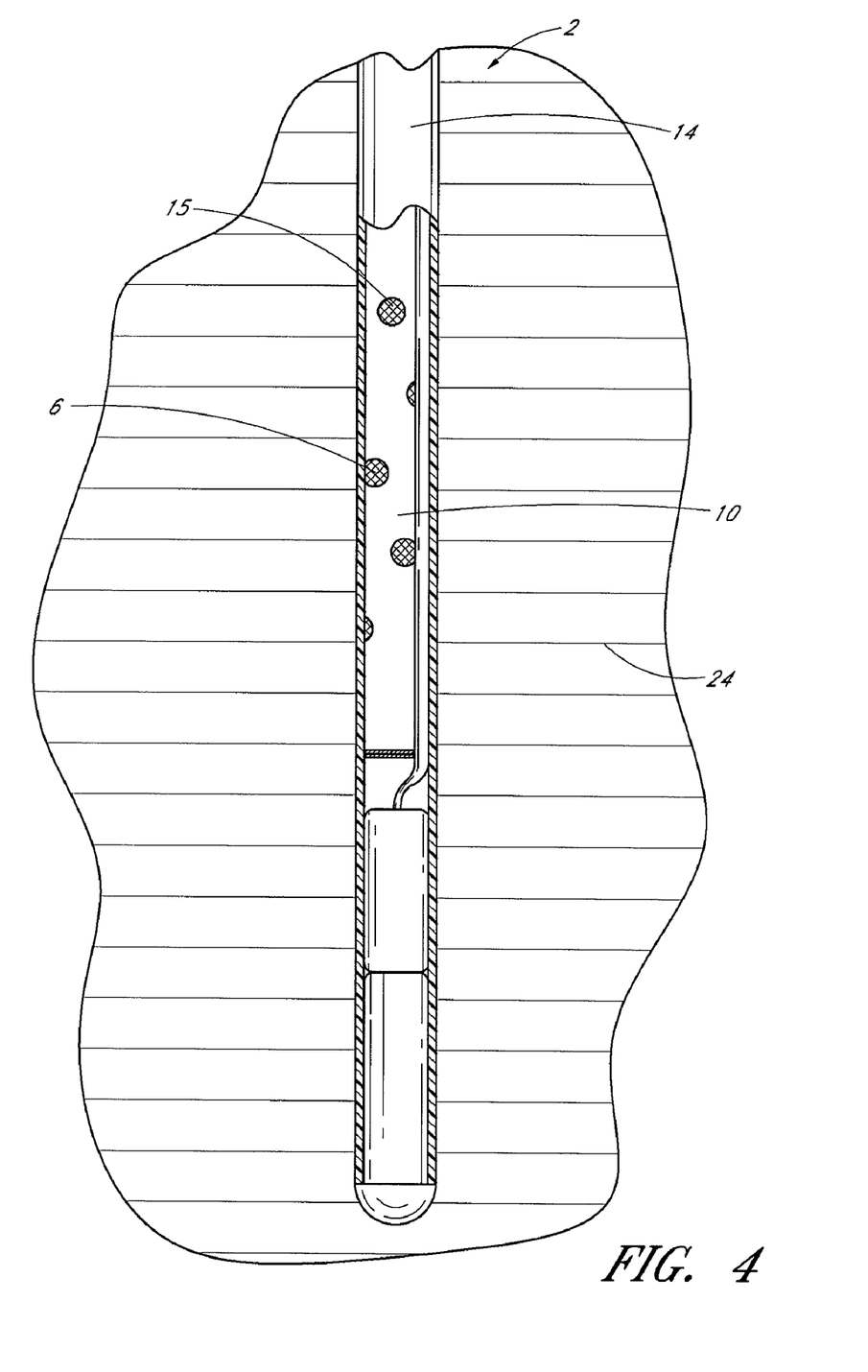
FIG. 4 is a cut-away view of the sensor shown in FIG. 1 disposed in a second solution.

In some embodiments as shown in FIG. 4, after the sensor 2 is filled with the first solution 15, the optical fiber 10 and the first solution 15 filled porous membrane sheath 14 and cavity 6 are transferred to and immersed into a second solution 24 comprising a second initiator. In some embodiments, the second solution 24 is aqueous and the second initiator is tetramethylethylenediamine (TEMED). In some embodiments, the second solution 24 further comprises the same fluorescent dye and/or quencher found in the first solution 15 and in substantially the same concentrations. By having the fluorescent dye and quencher in both the first solution 15 and the second solution 24, diffusion of fluorescent dye and quencher out of the first solution 15 and into the second solution 24 can be reduced. In some embodiments where a second solution 24 is used, the second solution 24 further comprises monomer in substantially the same concentration as in the first solution 15. This reduces diffusion of monomer out of the first solution 15 by reducing the monomer gradient between the first solution 14 and the second solution 24.

Figure 3A:
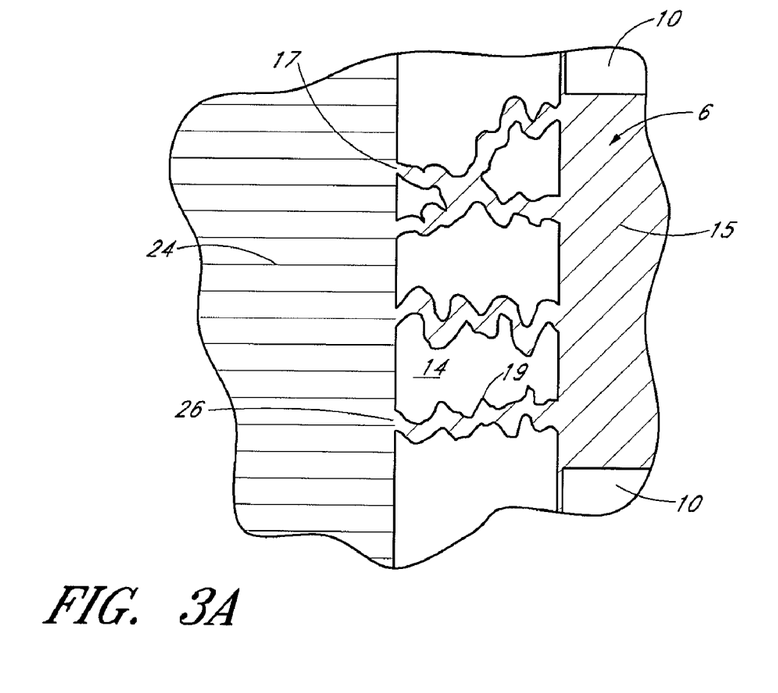
FIG. 3A is a cross-sectional view of a portion of the porous membrane sheath, optical fiber and cavity before polymerization.

In some embodiments as shown in FIG. 3A, at or approximately at the interface 26 between the first and second solutions 15 and 24, the first initiator and the second initiator can react together to generate a radical. In some embodiments, the first initiator and the second initiator react together in a redox reaction. In other embodiments, the radical can be generated by thermal decomposition, photolytic initiation or initiation by ionizing radiation. In these other embodiments, the radical may be generated anywhere in the first solution. Once the radical is generated, the radical can then initiate polymerization of the monomer and crosslinker in the first solution 15.

Figure 3B:
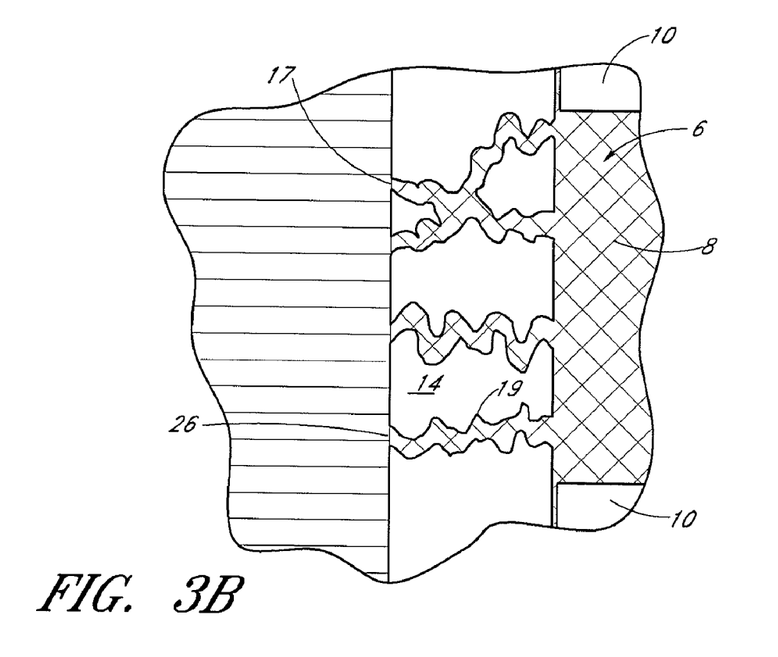
FIG. 3B is a cross-sectional view of a portion of the porous membrane sheath, optical fiber and cavity after polymerization.

As shown in FIG. 3B, when the radical is generated via a redox reaction as described herein, the polymerization proceeds generally from the interface 26 to the interior of the porous membrane sheath 14 and towards the cavity 6 in the optical fiber 10. Rapid initiation of polymerization at the interface 26 can help reduce the amount of first initiator that can diffuse from the first solution 15 and into the second solution 24. Reducing the amount of first initiator that diffuses out of the first solution 15 helps reduce polymerization of monomer outside the porous membrane sheath 14 which helps in forming a smooth external surface. Polymerization of the monomer and crosslinker results in a hydrogel 8 that in some embodiments substantially immobilizes the indicator system, forming the sensor 2.

In some embodiments, the first solution 15 is aqueous while the second solution 24 is organic. In some of these embodiments, the monomer is substantially soluble in the aqueous first solution 15 but is not substantially soluble in the organic second solution 24. Because the monomer is not soluble in the second solution 24, it will not diffuse into the second solution 24 and polymerization occurs within the first solution 15. Interfacial tension at the interface 26 between the first solution 15, the second solution 24 and the surface porous membrane sheath 14 can affect the amount of penetration of the organic second solution 24 into the pores 17 of the porous membrane sheath 14. Penetration of the second solution 24 into the porous membrane sheath 14 reduces the smoothness of the porous membrane sheath 14 after polymerization because the resulting hydrogel 8 is not flush with the opening of the pores 17.

In some embodiments, a surfactant that interacts with the surface of the porous membrane sheath 14 and the aqueous first solution 15 is added to the hydrophobic second solution 24. By changing the amount and type of surfactant added, the interfacial tension can be changed so that the interface 26 between the aqueous first solution 15 and the organic second solution 24 forms at the opening of the pores 17 in the porous membrane sheath 14. If the interface 26 forms at the opening of the pores 17, the resulting hydrogel 8 will be flush with the opening of the pores 17, resulting in a smooth surface.

In some embodiments, the porous membrane sheath 14 can be pretreated to change its hydrophilicity. Changing the hydrophilicity of the porous membrane sheath 14 changes the surface tension between the porous membrane sheath 14 and the first solution 15 and the second solution 24. For example, the porous membrane sheath 14 can be plasma etched to increase its hydrophilicity, which in some embodiments helps in maintaining the interface between the first solution 15 and the second solution at the opening of the pores 17.

In some embodiments having an organic second solution, the first initiator in the first solution 15 is a thermal initiator that generates radicals upon thermal decomposition. Use of a thermal initiator generally removes the need for a second initiator in the second solution 24. In some embodiments, the thermal initiator decomposes and generates radicals below a temperature of 55 degrees Celsius. Use of a thermal initiator is particularly suitable for thermally stable dyes, quenchers, monomers and crosslinkers.

Figure 5:
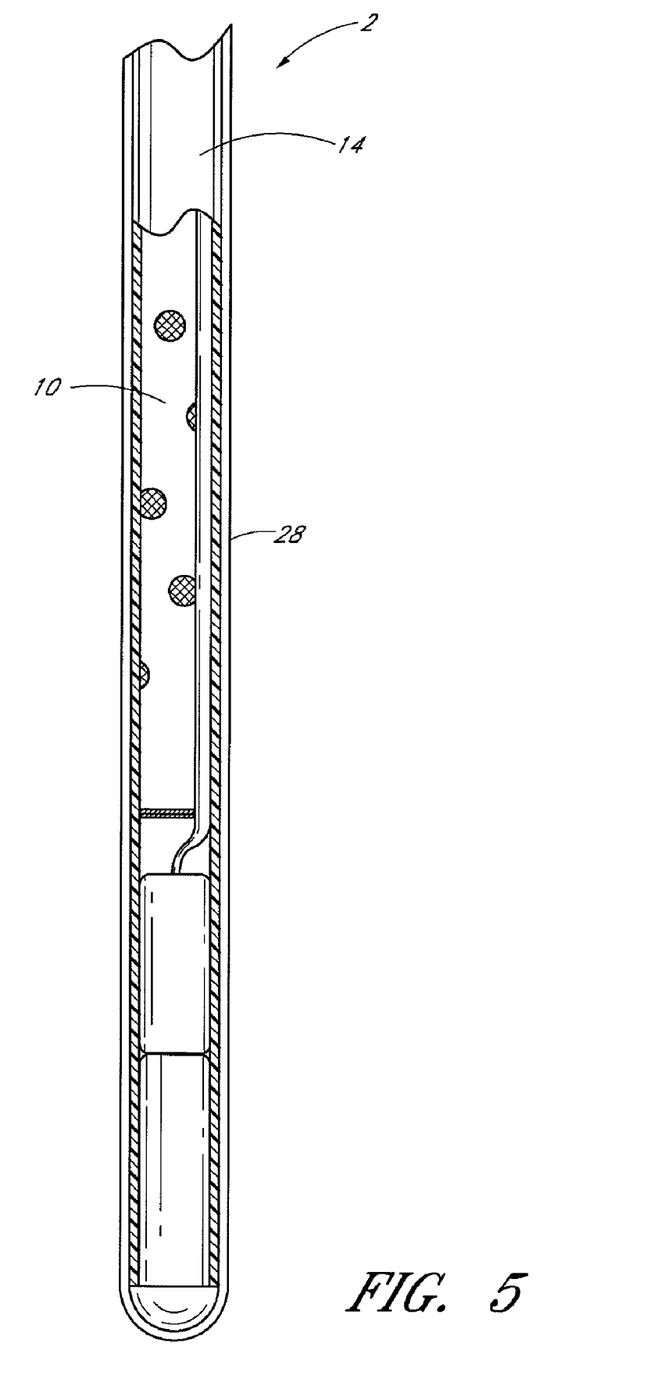
FIG. 5 is a cut-away view of the sensor shown in FIG. 1 covered with a coat of wax.

In some embodiments as shown in FIG. 5, in order to reduce water loss and to facilitate deoxygenation, after the porous membrane sheath 14 and cavity 6 are loaded with the first solution 15 comprising a thermal initiator, the porous membrane sheath 14 is coated with a wax 28. This can be accomplished by dipping the sensor 2 into liquid wax 28, which is allowed to harden around the porous membrane sheath 14.

In some embodiments, the wax 28 has a melting point above the thermal initiation temperature of the thermal initiator. Therefore, in order to reduce the likelihood of initiation during the wax coating process, the sensor 2 can be dipped and withdrawn from the liquid wax rapidly, thereby reducing the exposure of the initiator to the elevated temperature of the liquid wax 28. If desired, the sensor 2 comprising the first solution 15 and thermal initiator can be cooled or chilled so that the exposure to the hot wax 28 does not result in initiation and so the wax solidifies rapidly on the sensor surface. In addition, chilling the first solution 15 can be done during the loading of the first solution 15 into the sensor 2, which can be a relatively long process in some embodiments, thereby reducing the premature decomposition of the initiator which can result in early initiation of polymerization. Also, the thickness of the wax coating can be controlled in part by the temperature of the sensor 2 and/or the temperature of the liquid wax 28 when the sensor 2 is dipped into the liquid wax 28. The colder the sensor 2, the thicker the wax coating, and the hotter the liquid wax 28, the thinner the wax coating. After the coated sensor 2 is withdrawn from the liquid wax bath, the wax 28 is allowed to harden. In some embodiments, hardening of the wax coating can be facilitated by dipping the coated sensor 2 in a cold water bath. Additional coats of wax 28 can be put on the sensor 2 by simply dipping the wax coated sensor 2 into the liquid wax bath for an additional coat of wax.

In preferred embodiments, the coating of wax 28 is substantially impermeable to water and water vapor but permeable to oxygen. This reduces the loss of water from the first solution 15 that can occur though net diffusion of water or water vapor out of the first solution 15 while allowing the deoxygenation of the first solution 15.

In some embodiments, deoxygenation is performed by placing the wax 28 coated sensor 2 into an aqueous bath while bubbling a gas, such as nitrogen, in the bath. The oxygen in the first solution 15 diffuses into the bath and is carried away by the nitrogen gas. The aqueous bath can be made to have the same osmolarity and water vapor pressure as the first solution, thereby reducing the loss of water from the first solution 15 within the sensor 2. Because of the multiple measures used to reduce water loss out of the first solution 15, the sensor 2 can remain in the deoxygenation bath for extended periods of time, such as for example 1, 2, 4, 8, 12, 16 or 24 hours or more. In other embodiments, deoxygenation is substantially complete in less than 24 hours and therefore the next step in the polymerization process can be initiated in less than 24 hours. Deoxygenation reduces the formation of peroxides during the polymerization process which interfere with the polymerization of the monomer and the performance of the dye and quencher. In addition, because oxygen can function as an inhibitor of the polymerization reaction, the presence of oxygen in the first solution 15 can reduce the efficiency of the polymerization reaction by reducing the conversion of monomer into polymer and by inhibiting the initiation of the polymerization reaction.

In some embodiments, after the deoxygenation step, polymerization can be initiated by heating the sensor 2 and first solution 15 comprising the thermal initiator above the thermal initiation temperature but below the melting point of the wax. For example, in some embodiments, the sensor 2 is heated to 37 degrees Celsius for 24 hours. After polymerization of the hydrogel is complete, the wax can be removed from the sensor 2, e.g., by immersing in hexane and optionally including application of ultrasound energy. In other embodiments, a different solvent can be used instead of hexane. For example, other alkane hydrocarbons such as pentane and heptane and mixtures of these alkane hydrocarbons would also be suitable to remove the wax. In addition, it should be understood that a hexane solvent can comprise a mixture of hexane isomers, or more generally, an alkane solvent can comprise a mixture of the alkane isomers. The hexane wash and ultrasound may be repeated as necessary. The sensor thereby stripped of its wax coating is optionally transferred into an alcohol bath, and preferably finally to a water bath.

In another embodiment, the first solution 15 further comprises a second monomer that has at least one functional group. After polymerization into a hydrogel, different chemical moieties can be attached to the functional groups. Examples of chemical moieties with useful traits are molecules with anti-thrombogenic properties or anti-immunogenic properties.

In another embodiment, after the first solution 15 is loaded into the porous membrane sheath 14 and cavity 6, the optical fiber 10 and first solution 15 filled porous membrane sheath 14 are removed from the first solution 15 and polymerization is initiated in air without the use of a second solution 24. Photolytic initiation or ultraviolet light (UV) initiation can be used in these embodiments by selecting a photosensitizer or a UV initiator, as appropriate. Alternatively, in some embodiments, the monomer or crosslinker itself may generate radicals upon absorption of visible light or UV radiation. In some embodiments, it is desirable to have the air and first solution interface at the opening of the pores. In some embodiments, a surfactant is added to the first solution 15 so that the interfacial tension between the first solution 15 and the surface of the porous membrane sheath 14 results in the interface forming at the opening of the pores. Additionally, UV initiation may be combined with the wax coating procedure described above by selecting a wax that transmits UV. Additionally, UV initiation may be done with the use of a second solution 24. For example the second solution 24 may be chosen so as to minimize water loss during the UV polymerization process.

In some embodiments, the selection of monomer and crosslinker results in a polymer with acidic properties. For example, a monomer with an acidic functional group such as a phenol group can result in a polymer with acidic properties. In other embodiments, the selection of monomer and crosslinker results in a polymer with basic properties. For example, a monomer with a basic functional group such as an amine group can result in a polymer with basic properties. In additional embodiments, the selection of monomer and crosslinker results in a polymer with substantially neutral properties.

In some embodiments, polymerization is carried out at temperatures below 50° C. For dyes and quenchers that are unstable at high temperatures, polymerization at low temperatures is desirable. In other embodiments, polymerization is carried out at temperatures above 50° C. Polymerization at elevated temperatures is suitable for thermally stable dyes, quenchers, and reaction components.

In some embodiments, the first solution 15 is organic and the first initiator, the monomer and the crosslinker are soluble in organic solvents. In these embodiments, the second solution 24, if present, is aqueous in some embodiments and organic in other embodiments. By having an aqueous second solution 24, diffusion of organic soluble first initiator, monomer and crosslinker from the first solution 15 and into the second solution 24 is reduced. When the first solution 15 is organic, the method of polymerization is generally more flexible. For example, in some embodiments, polymerization proceeds as an addition reaction. In other embodiments, polymerization proceeds as a ring opening reaction or a condensation reaction. In some embodiments, radical polymerization is used, and in other embodiments anionic or cationic polymerization is used.

In some embodiments, the monomer is not polymerized in a solvent, but instead, undergoes bulk polymerization. In these embodiments, the monomer is generally a liquid and the initiator, crosslinker, dye and/or quencher are generally soluble in the monomer, allowing the polymerization to be carried out without a solvent.

In some embodiments, the monomers and/or crosslinkers polymerize to form a hydrophilic polymer. In other embodiments, the monomers and/or crosslinkers polymerize to form a hydrophobic polymer. In some embodiments, the polymer is gas permeable.

In some embodiments, the polymerization can be accomplished at a basic pH by using an appropriate initiator combination. For example in some embodiments, the first initiator is TEMED, which is basic, and the second initiator is ammonium persulfate. This is advantageous when the dye and quencher are more soluble at a basic pH.

In other embodiments, the polymerization can be accomplished at an acidic pH by using an appropriate initiator combination. For example in some embodiments, the first initiator is ascorbic acid, which is acidic, and the second initiator is ammonium persulfate. Another example would be to use ascorbic acid with Fenton's reagent, where Fenton's reagent comprises hydrogen peroxide and a ferrous salt. Another example of an initiator pair is t-butyl hydroperoxide and sodium formaldehyde sulfoxilate.

Figure 6A:
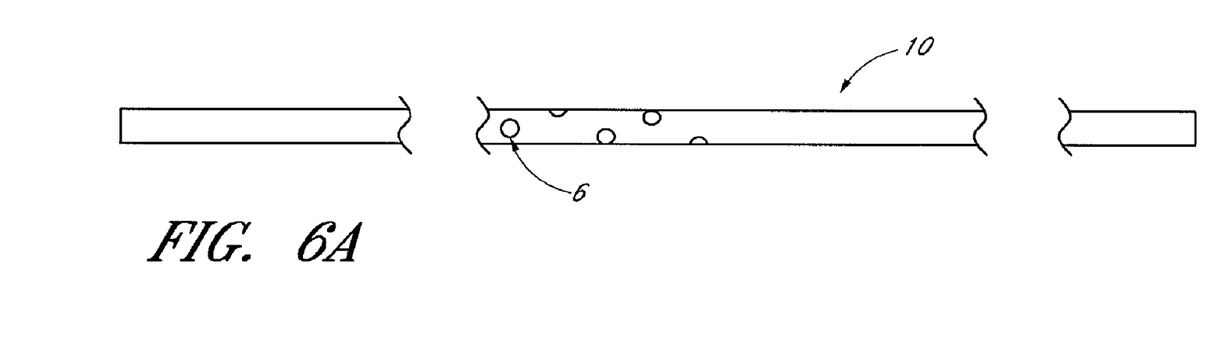
FIG. 6A is a side view of the optical fiber showing the arrangement of the cavities on the optical fiber.

In some embodiments as shown in FIG. 6A, the cavities 6 are cylindrically shaped holes that are spirally arranged on the optical fiber 10. The spiral arrangement of the cavities 6 can be accomplished by, for example, drilling a first cavity 6 in the optical fiber 10 along a transverse axis of the fiber 10, rotating the optical fiber 10 by a set amount between 0 and 360 degrees, and drilling the second cavity 6 distal the first cavity 6. To add an additional cavity 6, the fiber 10 is again rotated by the set amount and the additional cavity 6 is drilled distal the previous cavity 6. By offsetting the cavities 6, a more complete coverage of the cross-sectional area of the optical fiber 10 can be obtained, thus increasing the likelihood that excitation light passing through the optical fiber 10 will irradiate a sufficient and preferably an optimal amount of the indicator system immobilized within the hydrogel in the cavities.

In some embodiments, the cavity 6 is drilled completely through the optical fiber 10. In other embodiments, the cavity 6 is drilled partially through the optical fiber 10. In embodiments where the cavity 6 is drilled partially through the optical fiber 10, the cavity 6 can penetrate approximately halfway through the fiber 10, less than halfway through the fiber 10, and more than halfway through the fiber 10.

Figure 6B:
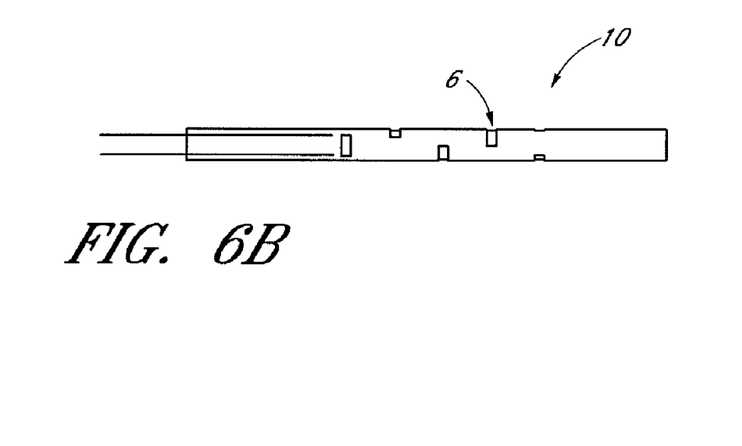
FIG. 6B is a side view of the optical fiber showing the arrangement of alternatively shaped cavities on the optical fiber.
Figure 6C:
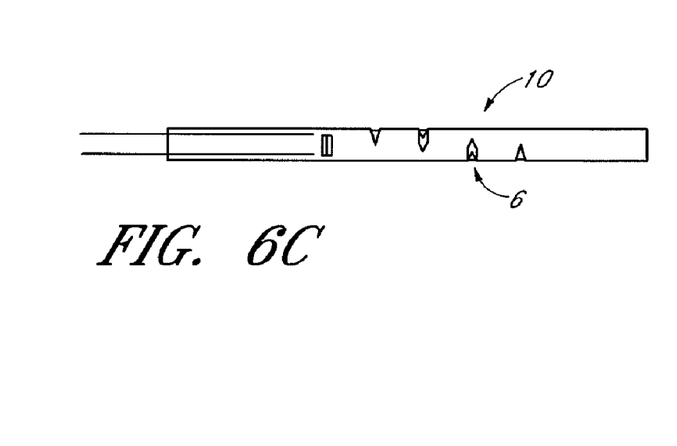
FIG. 6C is a side view of the optical fiber showing the arrangement of yet another alternatively shaped cavities on the optical fiber.

In some embodiments, the cavities 6 are not cylindrically shaped, but instead are rectangular-shaped as shown in FIG. 6B or wedge-shaped as shown in FIG. 6C. Other cavity 6 shapes are contemplated, such as hemispherical or a spiral or helical cut that winds longitudinally down the fiber 10, and the embodiments disclosed herein are not meant to be exhaustive. Indeed, any cavity geometries may be used in accordance with aspects of the invention.

While a number of preferred embodiments of the invention and variations thereof have been described in detail, other modifications and methods of using and medical applications for the same will be apparent to those of skill in the art. Accordingly, it should be understood that various applications, modifications, and substitutions may be made of equivalents without departing from the spirit of the invention or the scope of the claims.

What is claimed is:

1. A method for making an analyte sensor having a smooth outer surface, comprising:
   providing an optical fiber comprising a cavity covered by a membrane having pores;
   loading the cavity and the membrane pores with a solution comprising polymerizable monomers, an analyte indicator system and a polymerization initiator; and
   initiating polymerization of said monomers;
   wherein prior to initiating polymerization, the loaded cavity and membrane pores are coated with wax and the solution is deoxygenated.

2. The method of claim 1, wherein the wax coating is removed after polymerization is completed to leave a smooth outer surface, wherein the analyte indicator system is immobilized within the cavity.

3. The method of claim 2, wherein removing the wax comprises contacting the wax with an organic solvent.

4. The method of claim 3, wherein the organic solvent is an alkane.

5. The method of claim 4, wherein the alkane is hexane.

6. The method of claim 2, wherein removing the wax further comprises application of ultrasonic energy.

7. The method of claim 1, wherein the indicator system comprises a fluorophore and an analyte binding moiety.

8. The method of claim 1, wherein the loading step comprises vacuum filling.

9. The method of claim 1, wherein initiating polymerization comprises application of a second initiator selected to undergo a redox reaction with the polymerization initiator.

10. The method of claim 1, wherein initiating polymerization comprises application of thermal or radiation energy.

* * * * *